United States Patent [19]
Markland, Jr. et al.

[11] Patent Number: 5,814,609
[45] Date of Patent: Sep. 29, 1998

[54] COMPOSITIONS CONTAINING A DISINTEGRIN AND METHODS FOR ITS USE IN PREVENTING METASTASIS AND OTHER CONDITIONS

[75] Inventors: Francis S. Markland, Jr., Manhattan Beach; Qing Zhou, Alhambra, both of Calif.

[73] Assignee: University of Southern California, Los Angeles, Calif.

[21] Appl. No.: 745,603

[22] Filed: Nov. 8, 1996

Related U.S. Application Data

[60] Continuation-in-part of Ser. No. 632,691, Apr. 15, 1996, Pat. No. 5,731,288, which is a division of Ser. No. 540,423, Oct. 10, 1995, abandoned, which is a continuation of Ser. No. 141,321, Oct. 22, 1993, abandoned.

[51] Int. Cl.$^6$ .......................... A61K 38/00; A61K 38/16; C07K 14/00
[52] U.S. Cl. .............................................. 514/12; 530/324
[58] Field of Search ................................ 514/12; 530/324

[56] References Cited

PUBLICATIONS

Trikha M et al. Proc Annu Meet Am Assoc Cancer Res., 33, A199, Oct. 1992.
Dedhar S. et al. J. Biol. Chem., 264:4832–4836, Mar. 1989.
Bretti S. Int. J. of Cancer, 43:102–106, Jan. 1987.
Knudsen et al. Exper. Cell Research, 179:42–49, Jan. 1988.
Gehlsen et al. J. CELL Biol. 106:925–30, Mar. 1988.
Humphries et al. J. Clin. Investigation, 81, 7820790, Mar. 1988.
Dedhar et al. J. Cell. Biol. 105: 1175–1182, Mar. 1987.
Krontis. J. Molecular and cellular biology of acncer. In: Internal Medicine, 4th Edition, Editor–In–Chief Jay Stein, Chapters 71–72, pp. 699–715, Feb. 1992.
Brooks, P. C., et al., "Requirement of Vascular Integrin $\alpha_v\beta_3$ for Angiogenesis", *Science*, 264:569 (1994).
Brooks, P.C., et al., "Integrin $\alpha_v\beta_3$ Antagonists Promote Tumor Regression by Inducing Apoptosis of Angiogenic Blood Vessels", *Cell*, 79:1157 (1994).

*Primary Examiner*—Cecilia J. Tsang
*Assistant Examiner*—Michael Borin
*Attorney, Agent, or Firm*—Fulbright & Jaworski L.L.P.

[57] ABSTRACT

A disintegrin is employed as an active agent for treatment of various conditions, particularly cancer to prevent metastasis. In a particular embodiment contortrostatin is employed to prevent metastasis in breast cancer patients.

3 Claims, 11 Drawing Sheets

```
Contortro.     ----NP--DAAT-K---G-Q----L--D--LF---GTV--RARGDDLNDY-NGISAG-
cDNA deduced          NPCCDAATCKLTTGSQCADGLCCDQCKFMKEGTVCRRARGDDLDDYCNGISAGCPRNPFHA
Applagin       EAGEECDCGSPENPCCDAATCKLRPGAQCAEGLCCDQCKFMKEGTVC-RARGDDVNDYCNGISAGCPRNPFH
Trigramin      EAGEDCDCGSPANPCCDAATCKLIPGAQCGEGLCCDQCSFIEEGTVCRIARGDDLDDYCNGRSAGCPRNPFH
Albolabrin     EAGEDCDCGSPANPCCDAATCKLLPGAQCGEGLCCDQCSFMKKGTICRRARGDDLDDYCNGISAGCPRNPLHA
Elegantin      EAGEECDCGSPENPCCDAATCKLRPGAQCADGLCCDQCRFKKKRTICRRARGDNPDDRCTGQSADCPRNGLYS
Kistrin           GKECDCSSPENPCCDAATCKLRPGAQCGEGLCCEQCKFSRAGKICRIPRGDMPDDRCTGQSADCPRYH
```

FIG. 1

```
Contortro.    ----NP--DAAT-K---G-Q----L--D--LF---GTV--RARGDDLNDY-NGISAG-
cDNA deduced       NPCCDAATCKLTTGSQCADGLCCDQCKFMKEGTVCRRARGDDLDDYCNGISAGCPRNPFHA
Applagin      EAGEECDCGSPENPCCDAATCKLRPGAQCAEGLCCDQCKFMKEGTVC--RARGDDVNDYCNGISAGCPRNPFH
Trigramin     EAGEDCDCGSPANPCCDAATCKLIPGAQCGEGLCCDQCSFIEEGTVCRIARGDDLDDYCNGRSAGCPRNPFH
Albolabrin    EAGEDCDCGSPANPCCDAATCKLLPGAQCGEGLCCDQCSFMKKGTICRRARGDDLDDYCNGISAGCPRNPLHA
Elegantin     EAGEECDCGSPENPCCDAATCKLRPGAQCADGLCCDQCRFKKKRTICRRARGDNPDDRCTGQSADCPRNGLYS
Kistrin          GKECDCSSPENPCCDAATCKLRPGAQCGEGLCCEQCKFSRAGKICRIPRGDMPDDRCTGQSADCPRYH
```

FIG. 2-1

```
1    ATT CGG GGT CAA TAG AGG AAG AGC TCA AGT TGG CTT GAA AGC AGG AAG AGA TTG  54
     I   R   G   Q   *   R   K   S   S   S   W   L   E   S   R   K   R   L

55   CCT GTC TTC CAG CCA AAT CCA GCC GCC AAA ATG ATC CAG GTT CTC TTG GTA ACT  108
1                                                   M   I   Q   V   L   L   V   T    8

109  CTA TGC TTA GCA GTT TTT CCT TAT CAA GGG AGC TCT ATA ATT CTG GAA TCT GGG  162
9    L   C   L   A   V   F   P   Y   Q   G   S   S   I   I   L   E   S   G   26

163  AAC GTG AAT GAT TAT GAA GTA GTG TAT CCA CGA AAA GTC ACT CCA TTG CCC AAA  216
27   N   V   N   D   Y   E   V   V   Y   P   R   K   V   T   P   L   P   K   44

217  GGA GCA GTT CAG CCG AAG AAT CCG TGC GAT GCT GCA ACC TGT AAA CTG ACA      270
45   G   A   V   Q   P   K   N   P   C   D   A   A   T   C   K   L   T       62

271  ACA GGG TCA CAG TGT GCT GAT GGA CTG TGT TGT GAC CAG TGC AAA TTT ATG AAA  324
63   T   G   S   Q   C   A   D   G   L   C   C   D   Q   C   K   F   M   K   80

325  GAA GGA ACA GTA TGC CGG AGA GCA AGG GGT GAT GAC CTG GAT GAT TAC TGC AAT  378
81   E   G   T   V   C   R   R   A   R   G   D   D   L   D   D   Y   C   N   98

379  GGC ATA TCT GCT GGC TGT CCC AGA AAT CCC TTC CAT GCC TAA CCA ACA ATG GAG  432
99   G   I   S   A   G   C   P   R   N   P   F   H   A   *                  111

433  ATG GAA TGG TCT GCA GCA ACA GGC AGT GTG TTG ATC TGA ATA CAG CCT AAT AAT  486
```

FIG. 2-2

```
487  CAA CCT CTG GCT TCT CTC AGA TTT GAT CAT GGA GAT CCT TCT TCC AGA AGG TTT  540
541  CAC TTC CCT CAA ATC CAA AGA GAC CCA TCT GCC TGC ATC CTA CTA GTA AAT CAC  594
595  CCT TAG CTT CCA GAT GGT ATC CAA ATT CTG TAA TAT TTC TCC ATA TTT AAT      648
649  CTA TTT ACC TTT TGC TGT AAC AAA ACC TTT TTC CTG TCA CAA AGC TCC ATG GGC  702
703  ATG TAC AGC TTA TCT GCT GTC AAG AAA AAA AAT GGC CAT TTT ACC GTT TGC CAG  756
757  TTA CAA AGC ACA TTT AAT GCA ACA AGT TCT TCC TTT TGA GCT GAT GTA TTC AAA  810
811  GTC AAT GCT TCC TCT CCC AAA ATT TCA TGC TGG CTT CCC AAG ATG TAG CTG CTT  864
865  CCG TCA ATA AAC AAA CTA TTC TCA TTC AAA AAA AAA AAC CCG AAT TC  911
```

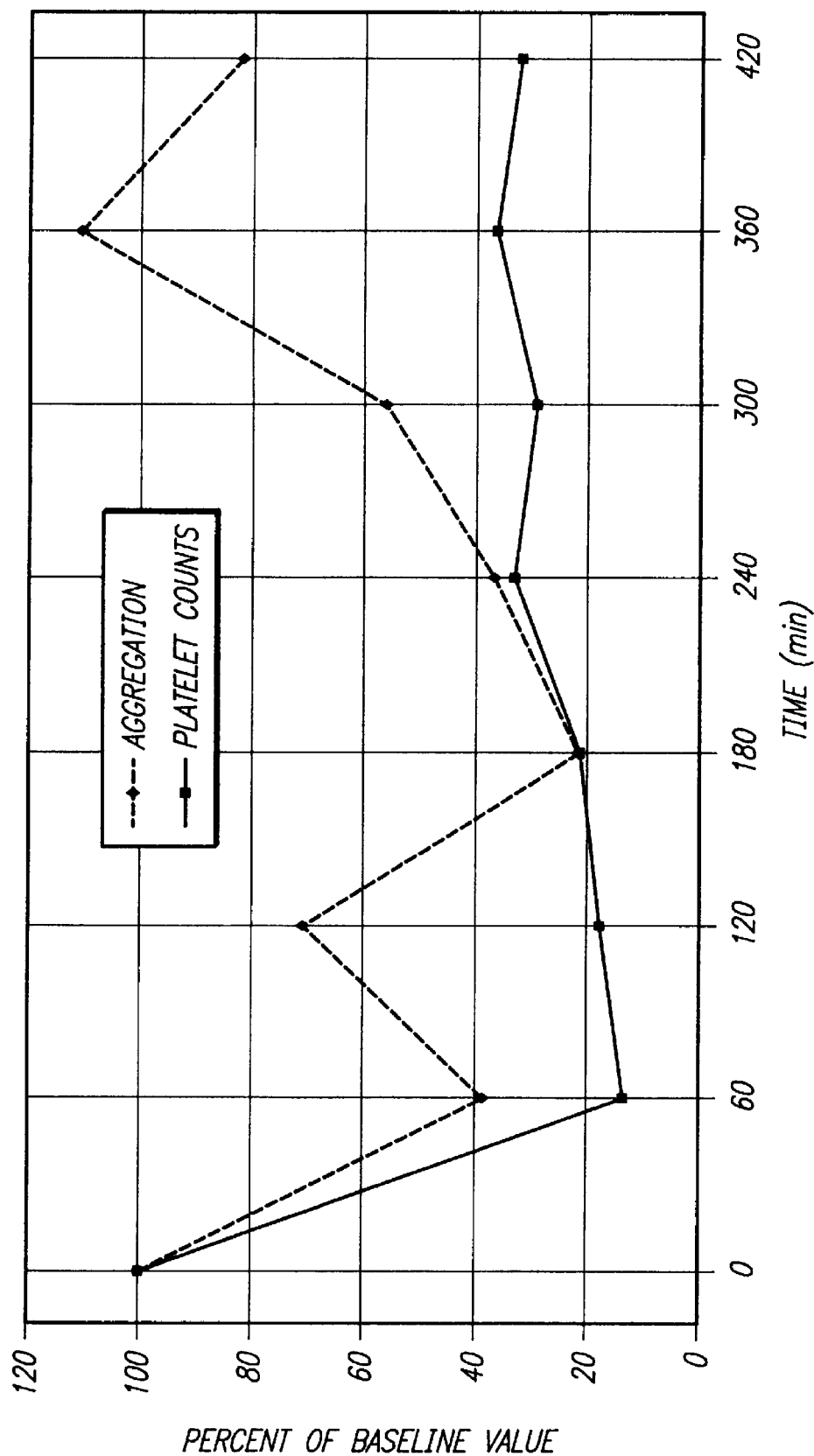

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 911 base pairs (111 amino acids)
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
ATT CGG GGT CAA TAG AGG AAG AGC TCA AGT TGG CTT GAA AGC AGG
                                                AAG AGA TTG CCT GTC    60
TTC CAG CCA AAT CCA GCC GCC AAA ATG ATC CAG GTT CTC TTG GTA
                        Met Ile Gln Val Leu Leu Val
                                          5
                                                ACT CTA TGC TTA GCA   120
                                                Thr Leu Cys Leu Ala
                                                             10
GTT TTT CCT TAT CAA GGG AGC TCT ATA ATT CTG GAA TCT GGG AAC
Val Phe Pro Tyr Gln Gly Ser Ser Ile Ile Leu Glu Ser Gly Asn
         15                  20                      25
                                                GTG AAT GAT TAT GAA   180
                                                Val Asn Asp Tyr Glu
                                                             30
GTA GTG TAT CCA CGA AAA GTC ACT CCA TTG CCC AAA GGA GCA GTT
Val Val Tyr Pro Arg Lys Val Thr Pro Leu Pro Lys Gly Ala Val
         35                  40                      45
                                                CAG CCG AAG AAT CCG   240
                                                Gln Pro Lys Asn Pro
                                                             50
TGC TGC GAT GCT GCA ACC TGT AAA CTG ACA ACA GGG TCA CAG TGT
Cys Cys Asp Ala Ala Thr Cys Lys Leu Thr Thr Gly Ser Gln Cys
         55                  60                      65
                                                GCA GAT GGA CTG TGT   300
                                                Ala Asp Gly Leu Cys
                                                             70
TGT GAC CAG TGC AAA TTT ATG AAA GAA GGA ACA GTA TGC CGG AGA
Cys Asp Gln Cys Lys Phe Met Lys Glu Gly Thr Val Cys Arg Arg
         75                  80                      85
                                                GCA AGG GGT GAT GAC   360
                                                Ala Arg Gly Asp Asp
                                                             90
CTG GAT GAT TAC TGC AAT GGC ATA TCT GCT GGC TGT CCC AGA AAT
Leu Asp Asp Tyr Cys Asn Gly Ile Ser Ala Gly Cys Pro Arg Asn
         95                 100                     105
                                                CCC TTC CAT GCC TAA   420
                                                Pro Phe His Ala
                                                            110
CCA ACA ATG GAG ATG GAA TGG TCT GCA GCA ACA GGC AGT GTG TTG
                                                ATC TGA ATA CAG CCT   480
AAT AAT CAA CCT CTG GCT TCT CTC AGA TTT GAT CAT GGA GAT CCT
                                                TCT TCC AGA AGG TTT   540
CAC TTC CCT CAA ATC AAA AGA GAC CCA TCT GCC TGC ATC CTA CTA
                                                GTA AAT CAC CCT TAG   600
CTT CCA GAT GGT ATC AAA ATT CTG TAA TAT TTC TTC TCC ATA TTT
                                                AAT CTA TTT ACC TTT   660
TGC TGT AAC AAA ACC TTT TTC CTG TCA CAA AGC TCC ATG GGC ATG
                                                TAC AGC TTA TCT GCT   720
GTC AAG AAA AAA AAT GGC CAT TTT ACC GTT TGC AGT TA CAA AGC
                                                ACA TTT AAT GCA ACA   780
AGT TCT TCC TTT TGA GCT GAT GTA TTC AAA GTC AAT GCT TCC TCT
```

-continued

```
                                                        CCC AAA ATT TCA TGC    840
TGG CTT CCC AAG ATG TAG CTG CTT CCG TCA ATA AAC AAA CTA TTC

TCA TTC AAA AAA AAA    900
AAC CCG AAT TC                                                                 911
```

COMPOSITIONS CONTAINING A DISINTEGRIN AND METHODS FOR ITS USE IN PREVENTING METASTASIS AND OTHER CONDITIONS

This application is a continuatio-in-part of U.S. Serial No. 08/632,691, filed Apr. 15, 1996, now U.S. Pat. No. 5,731,288, which is a division of application Serial No. 8/540,423, filed Oct. 10, 1995, now abandoned which is a continuation of application Ser. No. 8/141,321 filed Oct. 22, 1993, now abandoned.

FIELD OF THE INVENTION

The present invention relates generally to the field of biochemistry and medicine and in particular to compositions and methods for use in preventing metastasis and other conditions.

BACKGROUND OF THE INVENTION

Breast cancer is one of the leading causes of death among non-smoking women and the spread of the disease from the breast to distant sites is a major cause of death in breast cancer patients. At the time of diagnosis over 60% of breast cancer patients will have disease that has spread from the primary site in the beast to some distant site. Spread of cancer to remote sites, e.g. bone, lungs, liver, brain, i.e., metastasis, is a characteristic of malignancy and often leads to inoperable disease. Metastasis is the most common factor leading to death from breast cancer. Control of metastasis offers an important avenue for breast cancer treatment. Cancer cells metastasize through the blood or lymph vessels.

The first step of metastasis involves the attachment of cancer cells to tissues around the primary site, i.e., to the extracellular matrix (ECM) via cell surface integrins and other adhesion receptors. Integrins mediate cell-cell and cell-substratum interactions and are involved in bidirectional signaling that links the ECM with cytoskeletal proteins. Integrins play an important role in the interaction of mammary carcinoma cells with the ECM. In the second step, cancer cells secrete digestive enzymes that degrade the surrounding tissues allowing the tumor cells to invade these tissues. Eventually, the tumor cells enter the blood or lymphatic system where they repeat the adhesion and invasion steps at a distant (metastatic) site. At this remote site, tumor cells induce the formation of new blood vessels (a process called neovascularization), in and around the growing tumor. These new blood vessels supply nutrients to the metastatic tumor and allow it to grow. Treatments that block any of these steps should act to inhibit metastasis.

Integrins on cancer cells play important roles in tumor invasion and spread. They are a family of proteins found on the cell surface of many cell types that mediate interactions between cells, and between cells and their surroundings. Disintegrins bind to specific integrins on the surface of blood platelets, and blocks platelet aggregation wherein platelets adhere to one another. Platelets are small fragments of bone marrow cells that are found in the blood stream. They have both beneficial and harmful activities. Their useful action is to stop bleeding following injury by facilitating the formation of a blood clot. But, under certain conditions they are involved in blocking arteries that supply nourishment to the heart—an action that can lead to a heart attack.

Integrins are heterodimers composed of α and β submits that are non-covalently associated. They have been shown to be involved in cell-cell and cell-substratum interactions. They serve as receptors for extracellular matrix proteins such as fibronectin, fibrinogen, vitronectin, collagen and laminin. Some of these interactions have been shown to be mediated via an Arg-Gly-Asp (RGD) sequence present in the matrix proteins. Both the α and β subunits are required for fibrinogen binding. For example, one of the members of the superfamily of integrin cell surface receptors is the platelet membrane glycoprotein (GP)IIb/IIIa which interacts with plasma fibrinogen in platelet aggregation. The role of integrin cell surface receptors in platelet aggregation has been investigated in mediating coronary artery thrombosis and rethrombosis in the genesis of acute myocardial infarction [Zucker, M. B., *Sci. American* 242:86 (1990)]. For platelet aggregation an RGD sequence present in fibrinogen is essential for the interaction with GPIIb/IIIa [Ginsberg, M. H. et al., *Thrombos. Haemostas.* 59:1 (1988)]. Because of its inhibition of platelet aggregation, snake venom has been the subject of various investigations.

A number of proteins purified from venom of snakes of the Crotalidae and Viperidae families have been found to inhibit glycoprotein (GP) IIb/IIIa mediated platelet aggregation [see, e.g., Huang, T. F. et al., *J. Biol. Chem.* 262:16157 (1987); Gan, Z. R. et al., *J. Biol. Chem.* 263:19827 (1988); Yasuda, T. et al., *J. Am. Coll. Cardiol.* 16:714 (1990); Trikha, M. et al., *Fibtinolysis* 4 (Suppl. 1):105 (1990); Trikha, M. et al., *Blood* 76 (Suppl. 1):479a (1990); Holahan, M. A. et al., *Pharmacology* 42:340 (1991); Shebuski, R. J. et al., *Circulation* 82:169 (1990); Yasuda, T. et al., *Circulation* 83:1038 (1991)]. These proteins, classified as disintegrins, are typically disulfide rich. Moreover, all disintegrins isolated thus far, with the exception of barbourin [Scarborough, R. M. et al., *J. Biol Chem.* 266:9359 (1991)] contain an RGD (Arg-Gly-Asp) sequence that has been implicated as being involved in the inhibition of integrin-mediated interactions. In particular, the RGD sequence of the disintegrins may compete for fibrinogen binding sites of the platelet membrane, thereby inhibiting platelet aggregation induced by ADP or other agents.

Nonetheless, there appears to be increasing evidence that disintegrins may have unique surface geometry which facilitates interactions with integrins by mechanisms other than those based solely upon the RGD site. For example, the finding that a mutated, chemically synthesized derivative of echistatin (in which alanine was substituted for arginine in the RGD sequence) still possessed some biological activity, suggests that other regions in the protein may be involved in binding and that there may be some flexibility in the RGD binding site [Connolly, T. M. et al., *Circulation* 82 (Suppl. III):660 (1990)]. Synthetic RGD peptides, due to their small size, generally do not possess the molecular topography of the disintegrins and therefore cannot interact via the multiplicity of mechanisms likely to be involved in disintegrin binding.

In another investigation, prevention of reocclusion following thrombolysis using tissue-type plasminogen activator in a canine model system has been reported using either 30 μg/kg plus 3 μg/kg/min bitistatin, an 83 amino acid disintegrin derived from the venom of *Bitis arietans* [Shebuski et al., supra], or 15 μg/kg/min i.v. echistatin, a 49 amino acid disintegrin derived from the venom of *Echis cannatus* [Holahan et al., supra]. In the reported methods, an initial bolus of heparin (100 U/kg i.v.) and subsequent hourly boluses of 50 U/kg were used to increase activated partial thromboplastin times at least 1.5-fold over the control. Whereas it had previously been observed that heparin in combination with tissue-type plasminogen activator (tPA) did not affect the incidence of acute reocclusion in this model system, the addition of echistatin or bistatin lead to dramatic reductions in the incidence of acute thrombotic reocclusion. The administration of heparin was, however, apparently necessary for prevention of acute thrombotic reocclusion.

Similarly, kistrin (a 68 amino acid disintegrin derived from the venom 20 of *Calloselasma rhodostoma*) was evaluated in conjunction with recombinant tissue-type plasminogen activator in a canine model of coronary artery thrombosis with superimposed high grade stenosis [Yasuda et al. (1991), supra]. An effective dose of 4 µg/kg/min was determined to be sufficient to prevent reocclusion. Simultaneous systemic therapeutic heparin anticoagulation was used; the dose of heparin was selected to maintain the activated partial thromboplastin time more than two-fold throughout the experimental observation period.

U.S. Pat. No. 5,066,592 to Huang et al. describes the use of trigamin, a 72 amino acid disintegrin isolated from the venom of *Trimeresurus gramineus*, to inhibit fibrinogen binding to human platelets and thereby to inhibit fibrinogen-induced aggregation of human platelets. Trigamin is also reported to inhibit binding of von Willebrand factor to platelets. Trigamin is reported to inhibit $^{125}$I-fibrinogen binding to ADP (10 µmolar)-stimulated platelets in a concentration-dependent manner with an $IC_{50}$ of 2.8–5.6×10$^{-4}$M.

Isolation of an anti-platelet factor applaggin from the venom of *Agkistrodon piscivorus piscivorus* has also been reported [Chao, B. H. et al., *Proc. Natl. Acad. Sci.* USA 86:8050 (1989); Savage, B. et al., *J. Biol. Chemn.* 265:11766 (1990)]. Applaggin, unlike trigramin, is reported to inhibit dense-granule secretion in concert with inhibition of platelet aggregation in a dose-dependent manner. While initially described as a homodimer with at least two interchain disulifide bridges [Chao et al. (1989), supra], a subsequent report indicated that analysis of purified applaggin by mass spectroscopy showed the presence only of applaggin monomers with a mass of 7,666 Daltons and no evidence of dimerization [Wencel-Drake, J. D. et al., *Blood* 81:62 (1993)].

One disintegrin of particular interest is contortrostatin (CN), which has been isolated from the venom of *Agkistrodon contortrix contortix* (the southern copperhead snake). The originally-reported purification procedure included molecular sieve chromatography on Sephadex G-100 SF, desalting on Sephadex G-25F and reverse phase HPLC. ADP-enhanced aggregation of stirred human platelet rich plasma and the inhibition thereof by CN were monitored at 37° C. It was found that preincubation for 1 minute of the platelet rich plasma (3×10$^5$mm$^3$) with 5 µl of the low molecular weight peak after Sephadex G-100 SF resulted in 76% inhibition of platelet aggregation induced by 10 µM ADP [Trikha et al. (1990), supra].

In a subsequent report it was noted that in crude venom, the inhibitor was not readily detectable due to the presence of platelet aggregating activity; however, following the first step of purification (hydrophobic interaction HPLC) inhibitory activity was separated from both aggregating activity and an α-chain degrading fibrinolytic enzyme present in the venom. Inhibitory activity was pooled following HPLC and applied to a hydroxylapatite HPLC column. In the final step of purification, $C_4$ reverse phase HPLC chromatography was employed. The yield of the homogeneous protein was 3–5 mg per gram of venom. CN was reported to have a molecular weight of 18–21 kD under non-reducing conditions and 9 kD under reducing conditions; thus, the molecule was believed to be a homodimer with the two subunits being held together by disulfide bond(s). Isoelectric focusing showed that the protein had an acidic pI. CN was reported not to exhibit fibrinolytic activity and was not a 5'-nucleotidase or a phospholipase based on molecular size and kinetics of inhibition of platelet aggregation. Following preincubation for 1 minute, CN at approximately 100 nM was reported to completely inhibit ADP-induced platelet aggregation [Trikha et al. (1990), supra].

It has further been reported that CN has 70 amino acids with five to six disulfide bridges, and that the sequence of CN appears to begin 10 amino acids downstream of applaggin (a platelet aggregation inhibitor from the venom of *Agkistrodon piscivorus piscivorus*). It was speculated that CN may have an insertion and/or a C-terminal extension of nine amino acids. It was further reported that a 50% inhibition ($IC_{50}$) of human platelet aggregation in platelet rich plasma was observed at 0.8 µg/ml of CN, and at 2.2 µg/ml with canine platelets [Trikha, M. et al., *Journal of Cellular Biochem.* 16F:180 (1992)].

CN was reported to inhibit binding of human fibrosarcoma (HT-1080) and c-Ha-ras transfected rat embryo (4R) cells to fibronectin coated plates but not to matrigel coated plates. Inhibition of 4R cell binding to fibronectin in the presence of CN at 1 µg/ml and 5 µg/ml was 46% and 88%, respectively, and for HT1080 cells inhibition was 89% and 85%, respectively [Trikha, M. et al., *Proceedings of the American Association for Cancer Research* 33:34 (1992)].

SUMMARY OF THE INVENTION

In accordance with the present invention, the unique properties of disintegrins are exploited in methods and compositions for the treatment of various conditions, particularly for preventing metastasis in carcinoma and melanoma patients. In specific embodiments the positions and methods are provided for preventing metastasis in breast cancer patients. In still further embodiments, we provide the protein contortrostatin from southern copperhead snake venom that possesses potent anti-tumor activity. A sophisticated technique has been developed to purify this protein from the complex mixture of proteins found in southern copperhead venom. As indicated above, originally CN was characterized as an inhibitor of platelet aggregation. We have purified several disintegrins from snake venoms. Disintegrins contain a constrained Arg-Gly-Asp (RGD) sequence at the tip of a flexible peptide loop protruding from the main protein core. This exposed RGD sequence enables disintegrins to bind to integrins with high affinity.

We have developed a metastatic breast cancer model by implanting human breast cancer cells into the mammary fat pads of mice. The mice we use were genetically manipulated so that their immune system is deficient and they are unable to reject the implanted human cancer cells. We observed that palpable tumor masses developed in the mammary fat pads two weeks after cancer cell implantation, and that tumor cells spread to the lungs in untreated animals within 12 weeks. CN or placebo was injected daily into tumors in several different groups of mice. Following treatment we found that the size of the tumor masses in the CN treated mice were significantly smaller than those in placebo-treated mice. Significantly, the CN-treated group showed >90% inhibition of tumor spread to other sites in the body, particularly the lungs, as compared to the placebo group. Our studies indicate that CN blocks the attachment of breast cancer cells to proteins which are essential components of blood vessel walls. CN also inhibited new blood vessel formation induced by breast cancer cells following incubation on a chick embryo membranous respiratory organ called the chorioallantoic membrane, while placebo treatment did not. Since neovascularization is critical to continued proliferation of a growing tumor 30 the ability to inhibit the growth of new vessels is an important anti-cancer action of CN.

Based on these studies it appears that disintegrins such as the snake venom protein CN possess anti-metastatic activity. Our findings suggest that CN blocks several critical steps in metastasis and is, therefore, more potent than other agents which only block a single step.

BRIEF DESCRIPTION OF THE DRAWINGS

The invention may be better understood with reference to the accompanying drawings, which include:

FIG. 1 shows a partial amino acid sequence of CN based on Edman degradation assay, compared with a cDNA deduced CN amino acids sequence along with other disintegrins illustrating common RGD sequences and highly conserved sequences on which PCR primers are designed;

FIG. 2 shows the nucleotide sequence of the full length of CN cDNA and the deduced amino acids;

FIG. 14 illustrates platelet counts and platelet aggregability as percent of the value at zero time in a canine treated with anisoylated plasminogen streptokinase activator complex (APSAC) and CN.

DETAILED DESCRIPTION OF THE INVENTION

Characterization of CN

Figure 3:
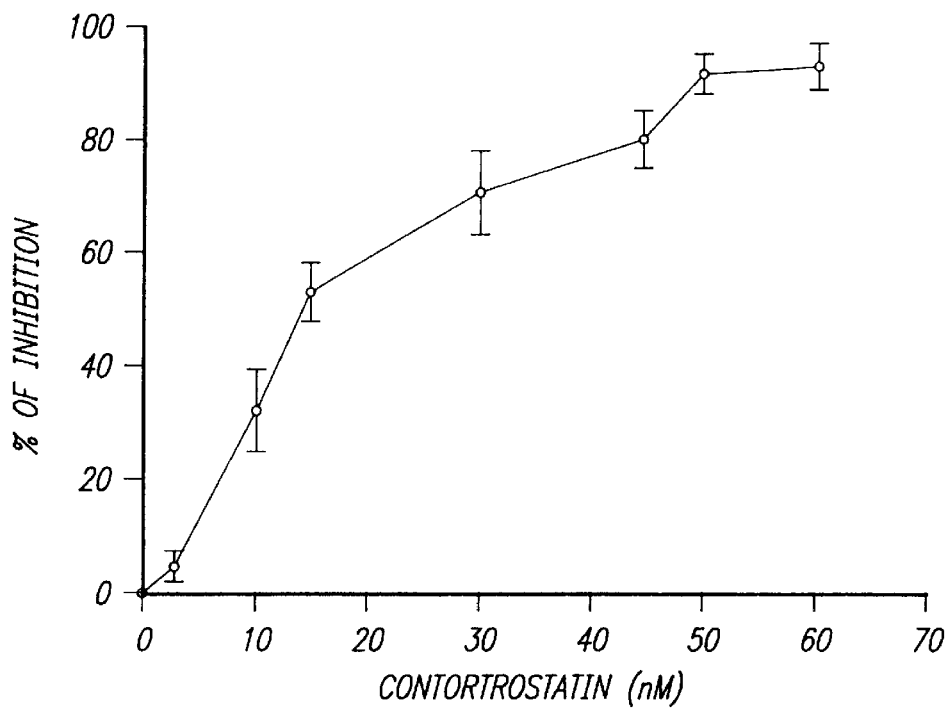
FIG. 3 shows CN inhibited adhesion of MDA-MB-435 to fibronectin.

We have purified and characterized the disintegrin CN from *A. c. contortrix* venom. CN is a homodimer with a mass of 13,505 for the intact protein and 6,956 for the reduced and pyridyletliylated protein. To test binding affinity to platelet GPIIb/IIIa (fibrinogen receptor), competition of CN with [$^{125}$I] 7E3, an antibody directed to GPIIb/IIIa, was analyzed using human platelet rich plasma (PRP). CN displayed IC$_{50}$ of 25 nM. Thus, CN 20 is a potent β3 integrin antagonist.

cDNA cloning of CN

The cDNA of CN has been amplified from a library of *A.c. contortrix* venom gland cells, constructed in λgt10. Amino acid component and partial amino acid sequences of CN precursor [seq ID NO=1] have been determined; see FIG. 2. The entire length of CN cDNA has been sequenced and is 911 nucleotides.

As a member of the disintegrin super family, CN shares high similarity with other disintegrins including trigramin whose nucleotide sequences were known. As shown in FIG. 1, a partial amino acid sequence of CN based on Edman degradation assay is compared with cDNA deduced CN amino acid sequence. These sequences are also compared with other disintegrins as indicated. The RGD sequence is bold-faced and the highly conserved sequences on which PCR primers are designed are underlined. See also FIG. 1 where the cDNA of CN has been cloned by means of PCR using primers based on the highly homologous sequences among the disintegrin family as well as known λgt10 sequences flanking the cDNA inserts. PCR primer pairs are: Primer 1 (λgt10 forward primer) and Primer 2: 5'-GTTTACAGGTTGCAGCATCGC-3', which is antisense of trigramin cDNA encoding part of the underlined conserved sequence (FIG. 1). Primers 1 and 2 amplify DNA coding amino acids upstream to the underlined part. Primer 3, which is complementary to Primer 2, and Primer 4 (λgt 10 reverse primer) amplify those coding the downstream part of CN. Full length cDNA has been obtained by overlapping extension of the two pieces of PCR products.

The extension product has been sequenced as indicated in FIG. 2. It is composed of an 84-nucleotide 5' non-coding region, an open reading frame (from ntd. number 85 to 421) coding for 111 amino acids, 3' non-coding region from nucleotide number 422 to 911, including an AATAAA site, and poly (A) sites. The coding region of the cDNA is made up of a 50-amino-acid-long signal peptide, and a 61 amino-acids mature protein with a calculated molecular weight of 6.77 kDa, which is equal to that of a CN subunit. DNA deduced amino acid sequences show high identity to the known partial sequence of CN and other disintegrins whose sequence are known as shown in FIG. 1. The cDNA deduced CN sequence possesess all the features of disintegrin: it contains the RGD sequence; the cysteine residues aligned perfectly with those of other disintegrins. Nest PCR amplifications were performed using the PCR overlapping extension product and the cDNA library as templates respectively. Both templates generated single product with identical molecular size. Sequencing of both PCR products revealed identical nucleotide sequence. This suggested that the overlapping PCR products represented the mature construction of CN cDNA. The full length cDNA fragment has been subcloned into a plasmid vector.

EXAMPLE 1

CN effects on Mammary Carcinoma Adhesion & Invasion

Figure 4:
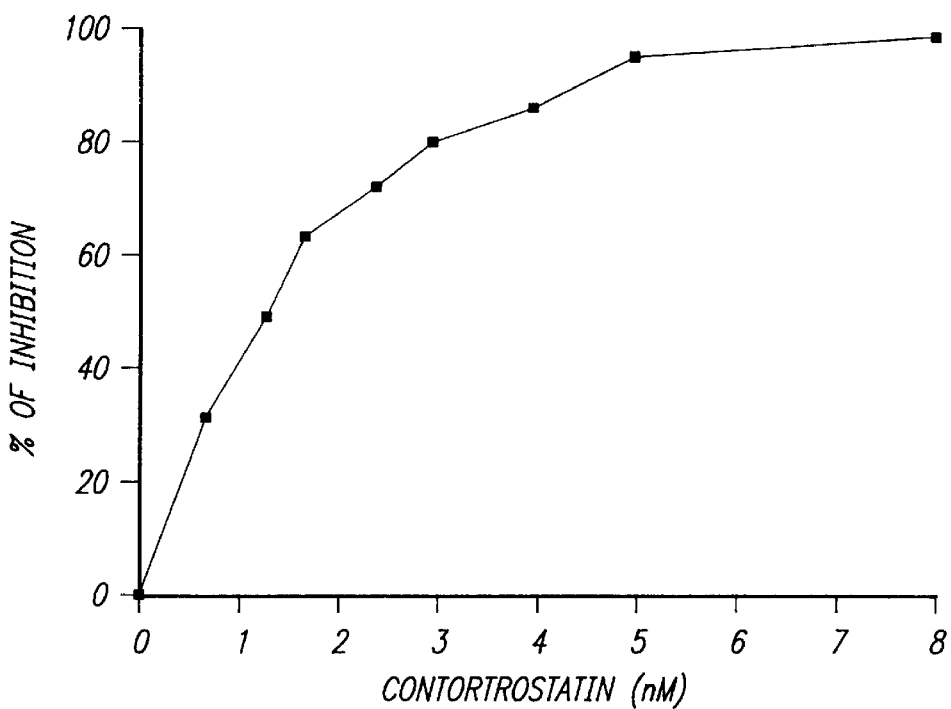
FIG. 4 shows CN inhibited adhesion of MDA-MB-435 to vitronectin.

The effect of CN on binding of highly metastatic human breast cancer cells, MDA-MB-435 cell line, to ECM proteins was examined. Human fibronectin and vitronectin were immobilized in the wells of 96-well microtiter plates. Referring to FIGS. 3 and 4, CN inhibited adhesion of MDA-MB-435 to both ECM proteins in a dose dependent manner. IC$_{50}$ for adhesion to fibronectin is 18 nM (FIG. 3) and for vitronectin the IC$_{50}$ is 1.5 nM (FIG. 4). CN had minimal effect on the weak adhesion seen by MDA-MB-435 cells to human type I collagen, or to rat type I collagen to which the MDA cells have a relatively strong affinity.

EXAMPLE 2

Figure 5:
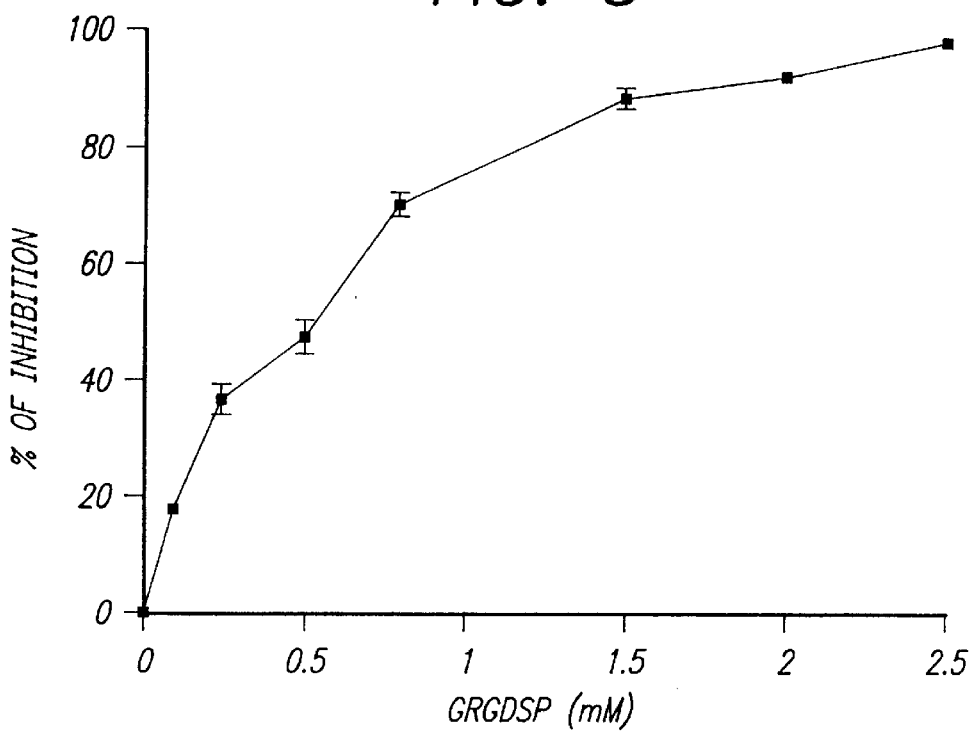
FIG. 5 shows the inhibition of binding of human mammary carcinoma cells to immobilized CN with GRGDSP.
Figure 6:
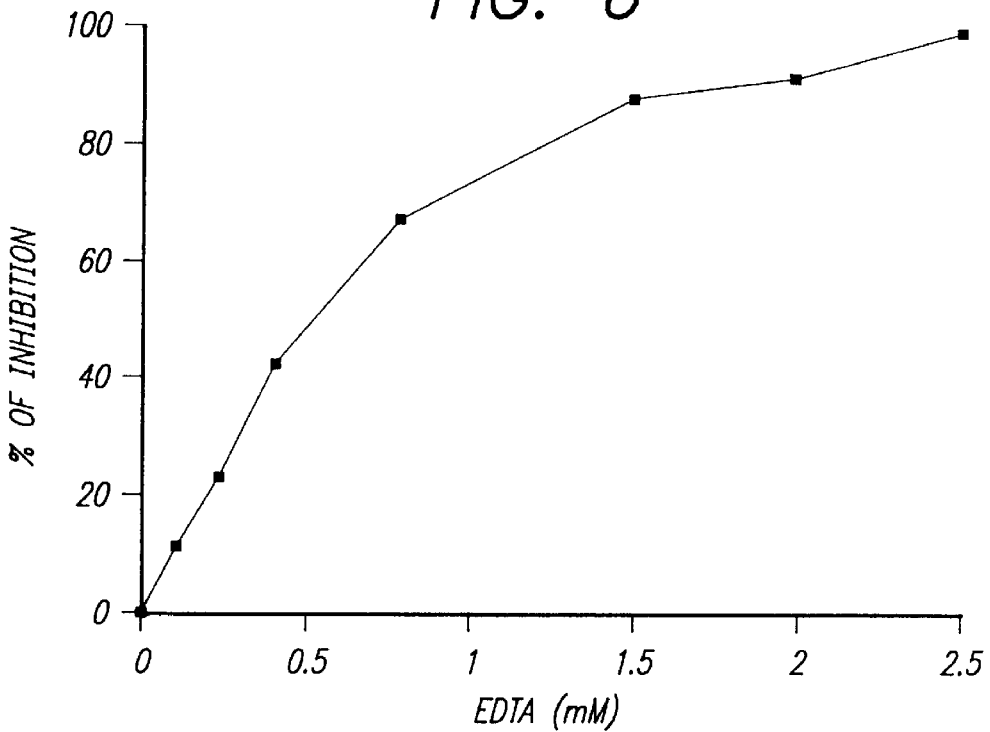
FIG. 6 shows the inhibition of binding of human mammary carcinoma cells to immobilized CN with EDTA.

In a variation of the above experiments, CN was immobilized. It was found that CN can support binding of MDA-MB-435 cells in a dose dependent manner. Binding of MDA-MB-435 cells to immobilized CN is blocked by an RGD peptide, GRGDSP ($IC_{50}$=0.4 mM), and by EDTA ($IC_{50}$=0.8 mM). Since integrin receptors require metal ions for non covalent association of their subunits, our findings indicate that CN binds to integrin receptors on the surface of MDA-MB-435 cells via an RGD-mediated mechanism. The finding that immobilized CN can support adhesion of MDA-MB-435 cells suggests that this binding involves cell surface receptors on the tumor cells. Referring to FIGS. 5 and 6, varying concentrations of GRGDSP (FIG. 5) or EDTA (FIG. 6) were used to inhibit binding of human mammary carcinoma cells to immobilized CN with CN at 0.1 µg/well. The vertical line at each data point indicates the y-axis error bar. All experiments were conducted as three sets of triplicates for each data point. Since adhesion of MDA-MB-435 cells to immobilized CN is completely blocked by GRGDSP and by EDTA as shown in FIGS. 5 and 6, CN binds solely to integrin receptors of MDA-MB-435 cells via an RGD dependent mechanism.

EXAMPLE 3

Figure 7:
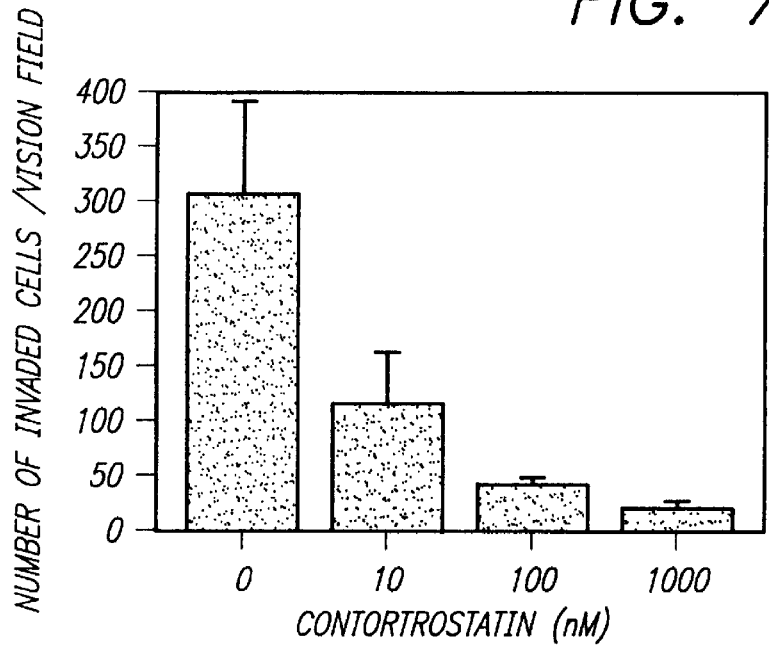
FIG. 7 shows the inhibition of invasion of MDA-MB-435 cells through a Matrigel coated invasion chamber.

Referring to FIG. 7, we have also demonstrated the inhibitory effect of CN on the invasion of a synthetic basement membrane by the MDA-MB-435 cells using a Matrigel-coated invasion chamber. $2.5 \times 10^3$ MDA-MB-435 cells treated with various concentration of CN were allowed to migrate across the Matrigel layer for 48 hrs. Assays at each CN concentration were performed in triplicate. Cells invaded through the Matrigel filter were fixed and stained. Invaded cells were quantitated with microscope by the mean of cell numbers in three randomly selected vision fields.

EXAMPLE 4

Figure 8:
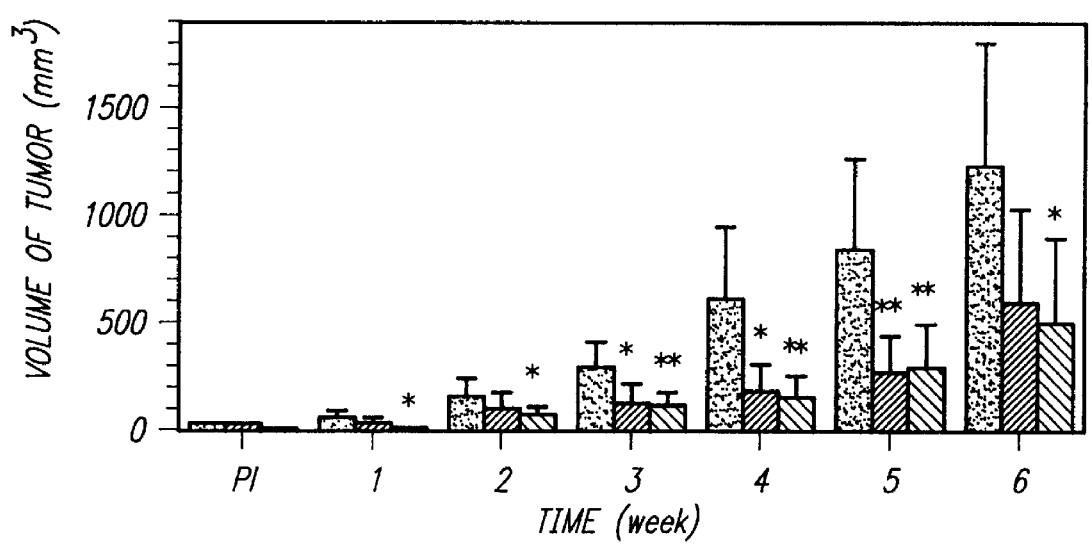
FIG. 8 shows the effect of CN on the growth MDA-MB-435 tumor in experimental nude mice.

CN Inhibits Growth and Metastasis of MDA-MB-435 Breast Cancer in Nude Mouse Experimental Model A spontaneous (orthotopic) metastatic model of nude mice has been established by implantation of MDA-MB-435 cells ($5 \times 10^5$ in 0.1 ml) in the mammary fat pads (mfp). Palpable tumors appeared by the 10th day post-implantation. Daily injections of CN into the tumor masses of each of the groups are carried out, started at the 14th day post-implantation. Tumors were removed by the 8th week post-implantation. The animals were allowed to survive for 2 more weeks without CN administration. The animals were then sacrificed and lung metastases were carefully examined. Referring to FIG. 8, our findings indicate that local injection of CN substantially inhibited the growth rate of the tumor. The volumes of tumor masses (mean±S.D.) of control (dark bars), low-dosage (0.5 µg/day, gray bars), and high-dosage (5 µg/gday, light gray bars) CN-treated group are shown. The seven clusters of bars from left to right represent the data of pre-injection (PI, 14th day post-implantation) and the 1st through 6th week of injection. Student t-tests were employed to test the significance of differences. The use of * and ** indicate P<0.05 and P<0.01, respectively.

The mean weight of tumors treated by high-dose CN (5 µg/day) is significantly lower than control group (P<0.05). Table I shows the incidence of lung metastasis based on gross examination and counting of surface nodules. Metastatic spread in the control group is much more extensive than the high dose CN group which showed >90% inhibition of metastasis. These data demonstrate the potential therapeutic role of CN in the treatment of human breast cancer.

TABLE 1

Effect of Contortrostatin on the Incidence of Metastatic MDA-MB-435 Breast Cancer In Nude Mouse Experimental Model.

| Groups | Metastasis Incidence | | | |
|---|---|---|---|---|
| | In situ relapse | Mean size of relapse tumor (mm³) | # of nodules in lung (median) | Other Organs[1] |
| Control | 4/5 | 66.7 ± 51.7 | 47.5[2] | 5/5 |
| CN (5 µg/day) | 2/6 | 48.7 ± 10.5 | 4.5 | 2/6 |

[1]Organs include: Chest wall, mediastinum, diaphragm, and pleurae.
[2]In 2/5 animals, lungs are directly invaded by cancer cells from pleurae and mediastinum.

EXAMPLE 5

CN Inhibits Angiogenesis Induced by MDA-MB-435 Tumor In CAM

Figure 9A:
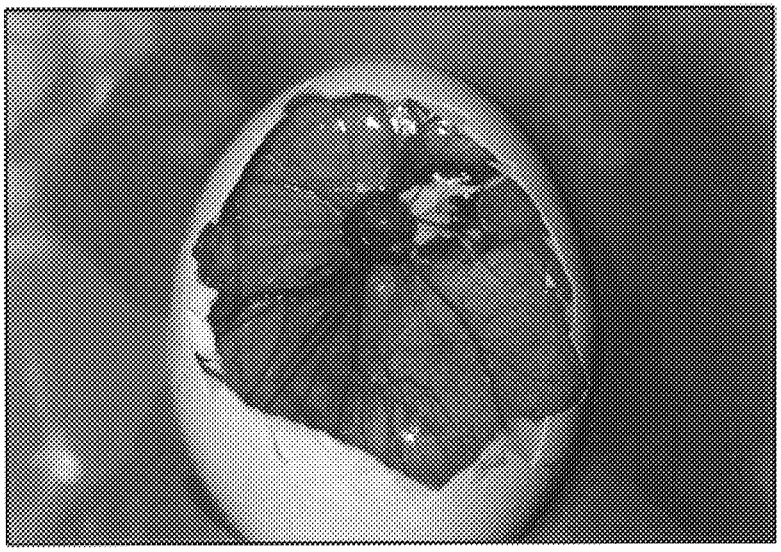
FIG. 9 are photographs demonstrating tumor induced angiogenesis in a control chick embryo chorioallantoic membrane (CAM) (A), CAM treated with 20 µg of CN (B), and CAM treated with 150 µg of CN (C)
Figure 9B:
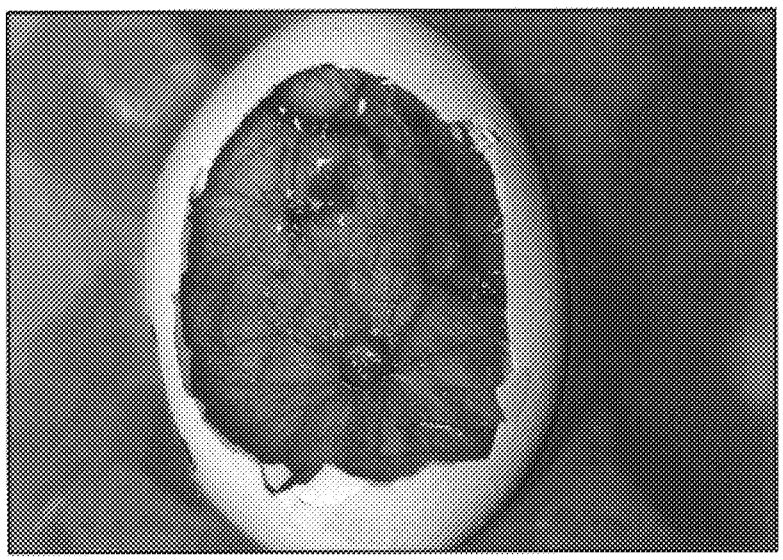
Figure 9C:
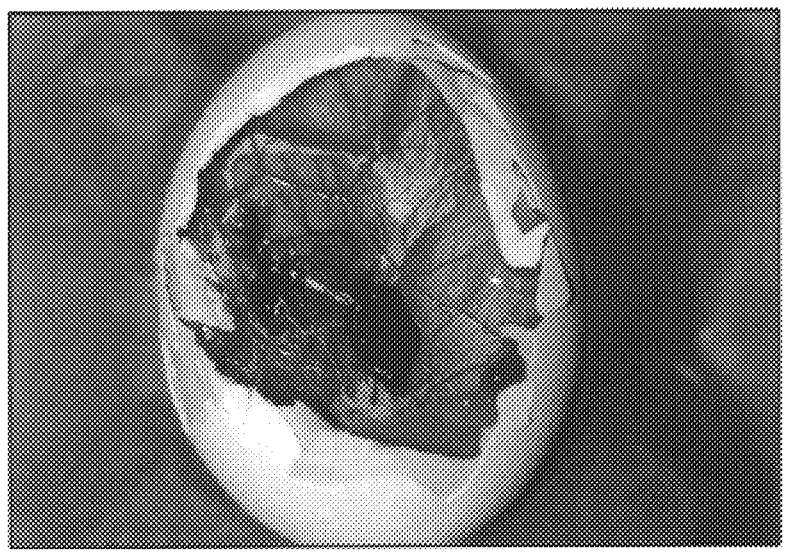

The hypothesis that inhibitory effect on the growth of the tumors probably results at least in part from the blockage of angiogenesis by CN has been preliminary verified by observing the effect of CN on tumor induced angiogenesis on chick embryo chorioallantoic membrane (CAM). MDA-MB-435 tumor masses were inoculated on CAM of 10-day chick embryos. CN at various dosages were injected intravenously into CAM on day 2 post-inoculation. Tumor induced angiogenesis and inhibitory effect of CN on angiogenesis can be easily observed in CAM after 3 days of incubation. As shown in FIG. 9, vessels are distributed in a convergent manner with the tumor mass in the center in the control embryo. Chick embryo is immunodeficient, and thus allows the growth of implanted MDA-MB-435 tumor. The embryos are incubated at 37° C. with humidity at 60%. CN at various dosages was injected intravenously into CAM on day 2 post-inoculation. Tumor induced angiogenesis on the 3rd day is demonstrated by the photo of FIG. 9. FIG. 9A is the control embyro. The vessels are distributed in a convergent manner with the tumor mass in the center. FIG. 9B is the CAM treated with 20 µg of CN. FIG. 9C is the CAM treated by 150 µg of CN. The 20 µg CN treated embryo vessels are thinner and less dense than the control; tumor mass is smaller than that on the control CAM. On the CAM treated by 150 µg of CN the vessels are even thinner and the convergent distribution pattern disappears completely, there is a necrotic tumor mass with volume significantly smaller than control and low dose CN, presumably due to the lack of blood supply (FIG. 9).

EXAMPLE 6

CN Has No Effect on Growth of MDA-MB-435 Cells In Vitro

Figure 10:
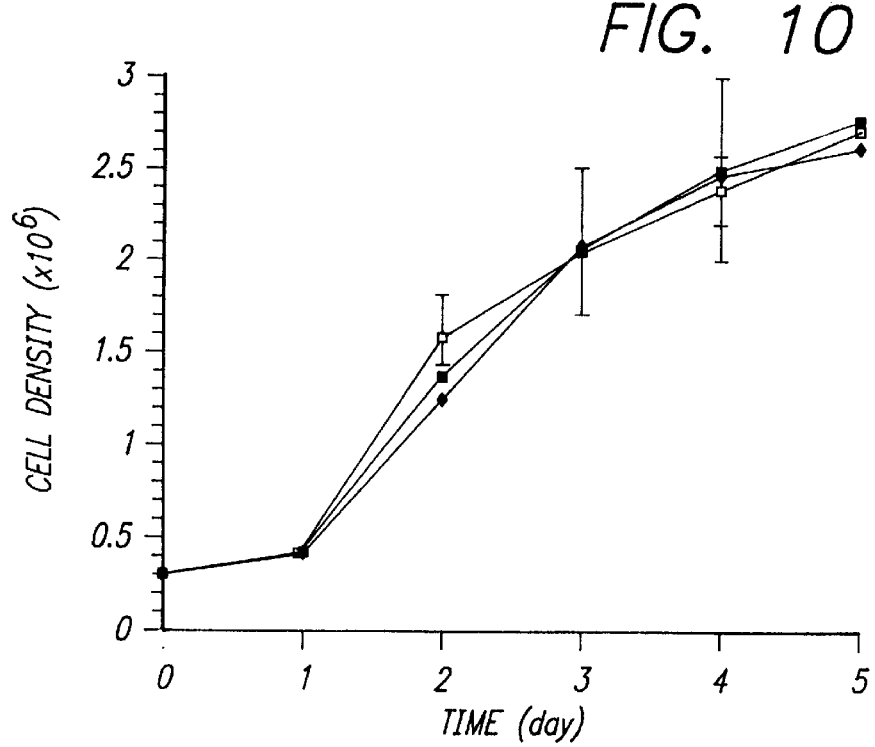
FIG. 10 shows the effect of CN on the proliferation of MDA-MB-435 cells in vitro.

MDA-MB-435 cells ($0.3 \times 10^6$/m]) were added to each well of a 6-well cell culture plates coated with 1/100 dilution of Matrigel. Cells were then treated with CN at various concentration. Growth curves of MDA-MB-435 cells in vitro without CN (circles), and with CN at 100 nM (triangles), and 500 nM (diamonds) are illustrated. Cell density was determined every 24 hours. Referring to FIG. 10, cells in the presence of CN proliferate equally well as control cells. The result indicate that CN has no direct cytotoxicity during in vitro culture of MDA-MB-435 cells.
CN Is Effective and Well Tolerated In Vivo It can be concluded from the chronic experiment with nude mice mentioned above that CN is not toxic. Despite its platelet aggregation inhibitory activity, no spontaneous hemorrhage is observed during the experiment. Prolonged bleeding at the injection sites in CN treated animals, however, was noticed.

CN is a novel antimetastatic agent. We hypothesize that CN blocks several critical steps (e.g. adhesion, invasion, angiogenesis) in cancer metastasis and progression. Therefore, it is more potent than other agents which block a single step.

Additional Embodiments

CN is clearly quite different from applaggin, as the latter has been demonstrated unmistakably to be a monomer [Wencel-Drake et al. (1993), supra]. Moreover, CN does not inhibit platelet release reactions, as has been demonstrated to be the case with applaggin in the aforementioned U.S. Pat. Nos. 5,182,260 and 5,196,403 to Maraganore et al. Finally, despite the similarities in sequence there are also significant differences between the sequences with respect to both the start site and some non-conserved amino acids.

CN has been found to be a potent inhibitor of human, rabbit and canine platelet aggregation in vitro. Unlike applaggin, however, CN does not inhibit platelet release reactions. Platelets comprise a plurality of different granules, including alpha granules and dense granules, whose contents are released when the platelets aggregate. The finding that CN does not inhibit platelet release of granule contents (including ATP from the dense granules) signifies that the platelets may still release their contents (and thus maintain some semblance of normal physiological activity) notwithstanding the inhibition of aggregation. By contrast, when applaggin inhibits platelet aggregation it also inhibits platelet release (as measured by, e.g., inhibition of serotonin release from the dense granules). Thus, normal platelet physiological processes are necessarily further perturbed with administration of applaggin.

Several lines of evidence indicate that CN inhibits platelet aggregation by binding specifically to the GPIIb/IIIa integrin receptor. For example, in a fibrinogen-GPIIb/IIIa ELISA [Dennis, M. S. et al., Proc. Natl. Acad. Sci. (USA) 87:2471 (1990)], in which the extent of purified GPIIb/IIIa bound to immobilized fibrinogen can be quantitated, CN effectively blocks GPIIb/IIIa binding. Additionally, the partial amino acid sequence of CN indicates considerable similarity with other disintegrins known to bind to GPIIb/IIIa. Finally, CN blocks 7E3 binding to GPIIb/IIIa. 7E3 is a murine monoclonal antibody that specifically binds to GPIIb/IIIa, thereby inhibiting human and canine platelet aggregation [Coller, B. S. et al., J. Clin. Invest. 72:325 (1983)]. In the presence of a low concentration of CN, 7E3 binding to platelets is significantly inhibited.

Three snake venom disintegrins, kistrin [Yasuda et al. (1990), supra], echistatin [Holahan et al. (1991), supra] and bitistatin [Shebuski, R. J. et al. (1990), supra], have demonstrated a potential role as antithrombotic agents for use in thrombolytic therapy by enhancing and sustaining arterial thrombolysis in conjunction with recombinant tissue plasminogen activator. Based on the low $IC_{50}$ values of CN, its in vivo efficacy as an antithrombotic agent has been examined. Using a canine reoccluding carotid arterial thrombosis model, CN has been found to efficiently sustain opening of the carotid artery in conjunction with anisoylated plasminogen streptokinase activator complex (APSAC). APSAC alone was found insufficient to prevent the rapid reocclusion of the carotid artery. Heparin was not needed to sustain opening when CN was administered with APSAC. This is a significant distinction over other disintegrins (e.g., echistatin, bitistatin and kistrin) which have been evaluated in models of coronary artery thrombosis.

The compositions of the present invention are particularly useful for treatment of thrombotic diseases in mammals, alone or in conjunction with one or more thrombolytic agents. In particular, the compositions of the present invention have utility in treating or preventing arterial, venous and microvascular thrombosis and thromboembolism. Thus, the compositions have utility in treating stroke, transient ischemic attacks, arteriosclerosis, atherosclerosis, pulmonary embolism, aneurisms and angina. In particular, the compositions have utility in preventing or treating myocardial infarctions.

The compositions of the present invention also have utility in inhibiting metastasis in melanoma and carcinoma patients. CN has been observed to bind to at least two sites on human melanoma M24met cells: a high affinity site with a dissociation constant (Kd) of 1.1 (±0.7) nM and 96,000 (±39,000) sites per cell; and a lower affinity site with a Kd of 41 (±13) nM and 480,000 (±90,000) sites per cell. Moreover, CN has been found to inhibit human melanoma M24met cell adhesion to fibronectin and vitronectin, and to a lesser extent to collagen and laminin. Thus, methods and compositions for preventing metastases in melanoma and carcinoma patients is also contemplated as within the scope of the present invention.

The disintegrin-containing compositions of the present invention are also useful in treatment of osteoporosis. Osteoclasts are multinucleated cells up to 400 $\mu$m in diameter which resorb mineralized tissue in vertebrates. Bone resorption appears to proceed by a combination of processes involving attachment to bone, polarized secretion of acid and proteases, and active motility of osteoclasts along the bone substrate; osteoclasts bind to bone via an RGD-sequence as an obligatory step in bone resorption, and this RGD-binding integrin is at adhesion structures [Sato, M. et al., J. Cell Biol., 111:1713 (1990)]. The molecular mechanisms whereby osteoclasts attach to bone are not well understood; however, by analogy to other cells, members of the integrin superfamily of divalent cation-dependent adhesion molecules are believed to mediate this interaction. Disintegrins, such as echistatin [Sato et al. (1990), supra] and presumably CN, inhibit bone resorption by isolated osteoclasts; the mechanism of action is presumably by disrupting adhesion structures. Accordingly, compositions and methods for treatment of osteoporosis employing an amount of CN effective to inhibit bone resorption by osteoclasts are also contemplated as within the scope of the present invention.

Finally, CN has utility in the promotion of wound healing. Events involved in wound healing are known to include alterations in integrin expression or functional activity and suggest that integrin receptor modulation plays a central role in wound repair and inflammation. Fibronectin is also known to play a number of roles in the wound healing process. Although fibronectin function is thought to be critical to effective wound healing, there are reports that at least one of its activities (the binding of bacteria) may be counterproductive [Grinnell, F., J. Cell Biochem. 26:107 (1984); Clark, R. A. F., Arch. Dermatol. 124:201 (1988)]; the presence of fibronectin in the wound bed may thus promote bacterial attachment and infection. Fibronectin also appears to be intimately involved in keloid formation. Keloids are a pathological consequence of wound healing that affects a significant proportion of non-caucasian patients. Keloids are benign tumors of connective tissue that grow beyond the boundary of the original wound and are rich in fibronectin and type I collagen [Sible, J. C. & Oliver, N., J. Cell Biochem. Suppl. 16F:170 (1992)]. By virtue of their inhibition of cell-cell and cell-extracellular matrix interactions (including interaction with fibronectin), disintegrins such as CN would be expected to have a profound effect on processes involved in wound repair, including keloid formation.

A major problem following obstetrical and gynecological surgery is the formation of adhesions. This widespread phenomenon observed in peritoneal wound repair is a leading cause of pain, intestinal obstruction and infertility. Adhesion formation appears to involve an imbalance in the fibrinolytic and fibroproliferative inflammatory responses and may also involve a modulation of the cell-cell or cell-extracellular matrix interactions. There is strong evidence for an important role of fibrin during the initial stages of adhesion formation [diZerega, G. S., *Prog. Clin. Biol. Res.* 381:1 (1993)]. The presence of cellular elements, including platelets, further exacerbates the role of fibrin. In view of the role of platelets and fibrin in adhesion formation, the use of disintegrins such as CN as a potential therapeutic agent is most attractive.

In preliminary studies in a rabbit model of adhesion formation, abrasion and devascularization of the uterine horns of rabbits were employed to induce adhesion formation during wound healing in untreated animals [Rodgers, K et al., *Int. J. Fertil.* 35:40 (1990)]. Alzet pumps were employed to continuously deliver CN at a rate of 10 μl/hr (36 μg/ml). In this model system, decreased adhesion formation was observed in treated animals compared to controls. Therefore, compositions and methods for preventing adhesion formation whereby an amount of CN effective to prevent adhesion formation is administered to a patient in need of such treatment are also contemplated as within the scope of the present invention.

As illustrated in the examples, CN may be isolated from the venom of *Agkistrodon contortrix contortrix* in a relatively straightforward manner. Alternatively, CN may also be prepared by exploiting a variety of biochemical methods in current use, such as recombinant DNA technology or the like. Thus, the purified protein may be sequenced (as is reported herein) and the sequence information used to deduce nucleotide sequences for making probes to identify the gene or genes that encodes a given protein. Once identified, the genes may be isolated and cloned into expression vectors. These vectors may be used to transform competent hosts to produce transformants that are capable of producing the snake venom protein.

Sources of DNA sequences encoding for the proteins include isolated DNA from suitable cells or cell lines, cloned DNA from a snake venom genomic library or cloned DNA from a complementary DNA (cDNA) library, where the total messenger RNA is reverse transcribed to DNA and cloned. Once a DNA sequence is identified which encodes for a protein of interest, the sequence of bases may be determined by known means [e.g., 20 Maxam and Gilbert, *Proc. Natl. Acad. Sci.* USA 74:560 (1977)]. In addition, recombinant DNA technology may be employed for obtaining expression. The DNA sequence may be analyzed and appropriate sites for cleavage defined. In this way, the sequence may be excised and introduced into a vector having the appropriate regulatory signals. A more detailed discussion of suitable techniques for identification and expression of disintegrin genes is provided in, e.g., U.S. Pat. Nos. 5,182,260 and 5,196,403 to Maraganore et al., the entire disclosures of which are hereby incorporated by reference.

Further, the sequence encoding the native protein may then be manipulated (for example, by single or multiple mutations or deletions) in a manner well known in the art to provide modified proteins, in which changes of one or more amino acids have been introduced. Following the procedures described herein, the determination of whether a particular polypeptide exhibits an activity profile characteristic of CN would then be a matter of routine experimentation. Accordingly, the present invention contemplates both the native CN and mutations thereof which exhibit the characteristic activity profile defined herein. Moreover, CN may also be employed in the form of a fusion protein with a suitable thrombolytic agent. Fusion proteins of this type may be prepared in a manner analogous to that described for formation of platelet aggregation inhibitor/anti-thrombin polypeptide fusion proteins in the aforementioned U.S. Pat. Nos. 5,182,260 and 5,196,403 to Maraganore et al.

The compositions of the present invention comprise at a minimum an amount of CN effective to achieve the desired effect (i.e., prevent metastasis in carcinoma patients, prevent thrombus formation, prevent adhesion formation, etc.) and a suitable carrier or excipient. Generally, in these compositions, CN is present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day.

When used to prevent thrombus formation, CN can be administered in combination with at least one thrombolytic agent present in an amount effective to achieve thrombolysis. Suitable thrombolytic agents include, but are not limited to, the following: anisoylated plasminogen streptokinase activator complex (APSAC); tissue-type plasminogen activator (tPA); urokinase-type plasminogen activator (uPA); and fibrolase, a snake venom fibrinolytic agent as described in U.S. Pat. No. 4,610,879 to Markland, Jr. et al.

CN may be administered by a variety of heretofore known means suitable for delivery thereof into the blood stream in substantial amounts. Intravenous administration of CN in a suitable liquid vehicle or excipient is presently contemplated as the preferred route of administration. CN is soluble in water, and may therefore be effectively administered in a suitable aqueous solution (e.g., phosphate buffered saline). Alternatively, CN may be administered as a parenteral suspension. As is well known in the art, adjuvants such as local anesthetics, preservatives, buffering agents, lubricants, wetting agents, colorants, flavorings, fillers and diluents may suitably be included in any of these formulations.

In conducting the following examples, lyophilized venom from Agkistrodon contortrix contortrix was obtained from Biotoxins, Inc., St. Cloud, Fla. All chemicals were of the highest grade available. Pierce protein assay kit using bicinchoninic acid was employed to determine protein concentrations [Smith, P. K. et al., *AnaL Biochem.* 150:76 (1985)].

For hydrophobic interaction (HIC)-HPLC a Perkin Elmer 410 LC pump was employed with a LC-95 UV/VIS detector. For reverse phase HPLC a Spectra Physics LC 8810 pump was employed with an SP 8450 UV/VIS detector. Absorbance for HIC-HPLC was monitored at 280 nm and for RP-HPLC at 215 nm. A polypropyl aspartamide (250×21 mm) column (Poly LC, Columbia, MD) was used for hydrophobic interaction HPLC. C18 (218TP54 and 218TP510) columns were used for reverse phase (RP) HPLC (Vydac, Hesperia, CA). For cation exchange chromatography a CM (carboxymethyl) 300 column (SynChrom, Inc., Lafayette, IN) was employed.

EXAMPLE 7

CN was purified from Agkistrodon contortrix contortrix (Southern copperhead) venom using a four step HPLC procedure. For the first step of purification crude venom (1 g) was dissolved in 0.1M phosphate buffer containing 1M ammonium sulphate, pH 6.8 (buffer A) and applied to the polypropyl aspartamide HIC-HPLC column. Elution was achieved as follows: 50 minutes isocratically with 100% buffer A; a linear gradient for 90 minutes to 0.1M phosphate, pH 6.8 (buffer B); 40 minutes isocratic at 100% buffer B. Fractions of 10 ml were collected in a Pharmacia Frac 100 fraction collector at 4° C. using a flow rate of 5 ml/min. Fractions containing platelet aggregation inhibiting activity were pooled and concentrated by ultra-filtration using an Amicon stir cell with a YM3 membrane. Proteins were detected at 280 nm; platelet aggregation inhibiting activity was not observed in the flowthrough.

Further purification was achieved by C18 RP-HPLC. Fractions containing platelet aggregation inhibiting activity were pooled and concentrated for this second step. The C18 column (218TP510) was equilibrated with 95% of 0.1% TFA in water (solvent A) and 5% of 80% acetonitrile in 0.1% TFA in water (solvent B). Elution was achieved as follows: isocratic at 95% solvent A and 5% solvent B for 10 minutes; a linear gradient to 40% solvent B in 65 minutes; linear gradient to 100% solvent B in 20 minutes; isocratic at 100% solvent B for 25 minutes. Fractions were collected manually every minute at a flow rate of 7 ml/minute. CN eluted at 28% acetonitrile (66 minutes).

Fractions containing platelet aggregation inhibiting activity were pooled and rerun on the same C18 RP-HPLC column using a shallower gradient. Elution was achieved as follows: isocratic at 80% solvent A and 20% solvent B for 20 minutes; a linear gradient to 30% solvent B over 90 minutes; and a 25 minute linear gradient to 100% solvent B. CN eluted as a sharp peak at 22% acetonitrile (82 minutes). The minor peak eluting just before CN also contained platelet aggregation inhibiting activity and had a similar molecular weight to that of CN; due to the low yield, this peak was not further characterized.

A final purification step was performed using pooled fractions from the previous step. These pooled fractions were applied to a cation exchange, CM300, HPLC column and elution was achieved by an increasing gradient of sodium chloride. CN elutes at 52.5 minutes (160 mM NaCl). This step achieved a separation of CN from isoforms thereof. Yields of 1–2 mg of the four-step purified CN were obtained per gram of crude venom.

For SDS-polyacrylamide gel electrophoresis (SDS-PAGE) Tris-Tricine 16.5% gel was used according to published protocols under reducing and non-reducing conditions [Schagger, H. & Von Jagow, G., *Anal Biochem.* 166:368 (1987)]. The gel was run using a BioRad minigel system and stained with silver [Morrisey, J. H., *Anal Biochem.* 117:307 (1981)] or Coomassie blue R250.

SDS-PAGE analysis of CN revealed that it has a molecular mass of approximately 15,000 Daltons under non-reducing conditions and 5,000–7,000 Daltons under reducing conditions. This strongly suggests that CN is composed of two subunits. Another possibility, albeit unlikely, is that the large difference in migration may be attributed to differential uptake of SDS under non-reducing and reducing conditions.

The molecular weight of CN was confirmed by mass spectrometry using a triple quadrupole instrument with an electrospray ion source. A mass of 13,507 Daltons was determined for intact CN; the analysis also indicated a high degree of purity. Mass spectrometry of the reduced and pyridylethylated protein gave a mass of 7,996 Daltons. This is the expected value for the individual chains of a homodimer of this molecular weight, taking into account the incorporation of approximately 1,000 mass units for the 10 to 12 pyridylethyl groups incorporated into the 5–6 reduced disulfide bounds (based on homology with known disintegrins, there should be 5–6 disulfide bonds). These findings place CN in a unique position among all the disintegrins reported to date in that it exists as a dimer. Scatchard analysis of CN binding to unactivated human platelets revealed a single class of binding sites with a dissociation constant ($K_d$) of 25 nM and number of binding sites ($B_m$) equal to 100,000 per platelet. Reduction of the disulfide bonds in CN completely eliminated platelet aggregation inhibitory activity, even at concentrations ten times the $IC_{50}$, suggesting that structural parameters are critical for maintaining activity.

EXAMPLE 8

Column fractions obtained during purification were assayed for activity using fresh human platelet rich plasma (PRP) prepared from blood obtained from human volunteers who had had no medication for at least two weeks. Blood (36 ml) was drawn into 4 ml of 0.1M citrate and centrifuged at 150×g for 20 minutes. The supernatant, PRP, was removed and the remaining blood was centrifuged at 10,000 RPM to obtain platelet poor plasma (PPP). Platelet counts were adjusted to 250,000 platelets/μl using a Coulter counter. A Helena four channel aggregometer was used to monitor platelet aggregation. Inhibition of ADP-induced platelet aggregation was monitored at 37° C. by adding venom fractions one minute prior to the addition of ADP (10–20 μM final concentration). Fractions exhibiting platelet aggregation inhibiting activity were pooled and further purified. Rabbit and canine PRP was prepared by the same procedure and used in the studies described below.

Figure 11:
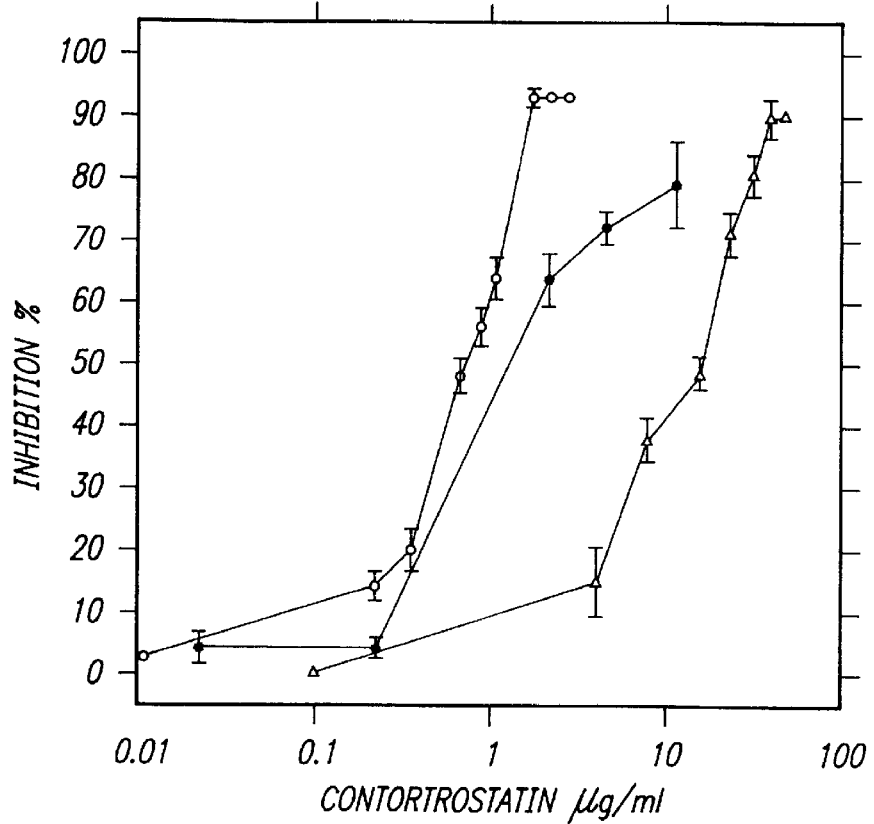
FIG. 11 illustrates the results of determinations of CN inhibition of human, canine and rabbit platelet aggregation.

CN inhibited ADP-induced platelet aggregation in human, canine, and rabbit PRPs (FIG. 11). Empty circles represent human platelet rich plasma, solid circles represent canine PRP, and empty triangles represent rabbit PRP. Varying concentration of CN were preincubated for one minute with PRP prior to the addition of ADP. CN (0.73 μg/ml) inhibited 10 μM ADP-induced human platelet aggregation by 50% ($IC_{50}$ equals 49 nM). The $IC_{50}$ for 20 μM ADP-induced canine platelet aggregation was 1.8 μg/ml for CN. Interestingly, the $IC_{50}$ for CN mediated inhibition of rabbit platelet aggregation was considerably higher; the $IC_{50}$ for 20 μM ADP-induced rabbit platelet aggregation was 17.3 μg/ml (1,150 nM) for CN.

EXAMPLE 9

Measurement of GPIIb/IIIa Specific Binding

Measurement of CN binding to platelet GPIIb/IIIa receptor was carried out using PRP prepared from blood obtained from human volunteers or male mongrel dogs. PRP was prepared as described above and the platelet count was determined with a H-10 cell counter (Texas International Laboratories, Inc., Houston, Tex.). PRP (180 μl) was incubated with 20 μl of varying concentrations of CN at room temperature. Radiolabelled antibody ($^{125}$I-7E3 IgG, 20 μl, 18 mg/ml, 80,000 cpm), specific for GPIIb/IIIa, was then added and the mixture incubated for 30 minutes. To establish equilibrium binding, 50 μl aliquots of the binding assay mixture were layered over 200 μl of 30% sucrose in 0.4 ml microcentrifuge tubes and spun at 10,000 RPM for 4 minutes in a swinging bucket rotor to separate platelet-bound antibody from free antibody. The pellet and the supernatant were separated and counted in a Packard Minaxi 5000 series gamma counter. The number of molecules of $^{125}$I-7E3 bound per platelet in the presence and absence of CN was calculated by using the following formula:

$$\frac{(4) \times 0.9 \, \mu g \, 7E3 \times 3.76 \times 10^{12} \, \text{molecules} \, 7E3/\mu g}{(5)}$$

wherein (1)=Pellet counts; (2)=Supernatant counts; (3)=Total CpM (1)+(2); (4)=Fraction bound (1)/(3); and (5)=Platelet counts per $\mu l \times 45 \, \mu l$.

Figure 12A:
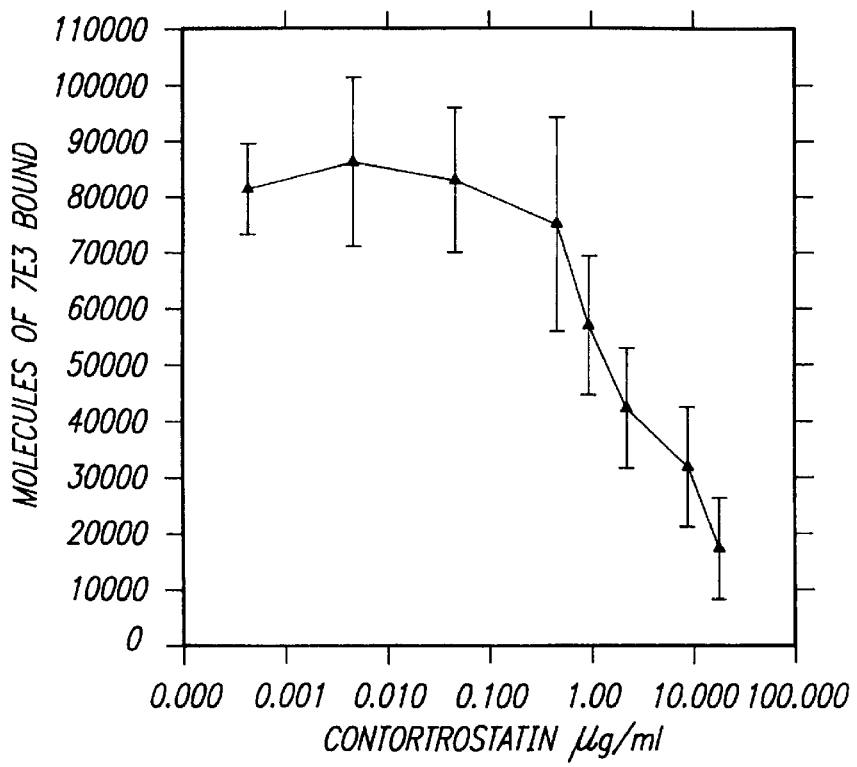
FIGS. 12A and 12B illustrate the results of binding studies of CN to human (FIG. 2A) and canine (FIG. 2B) GPIIb/IIIa in the presence of a fixed saturating concentration of murine monoclonal antibody 7E3.
Figure 12B:
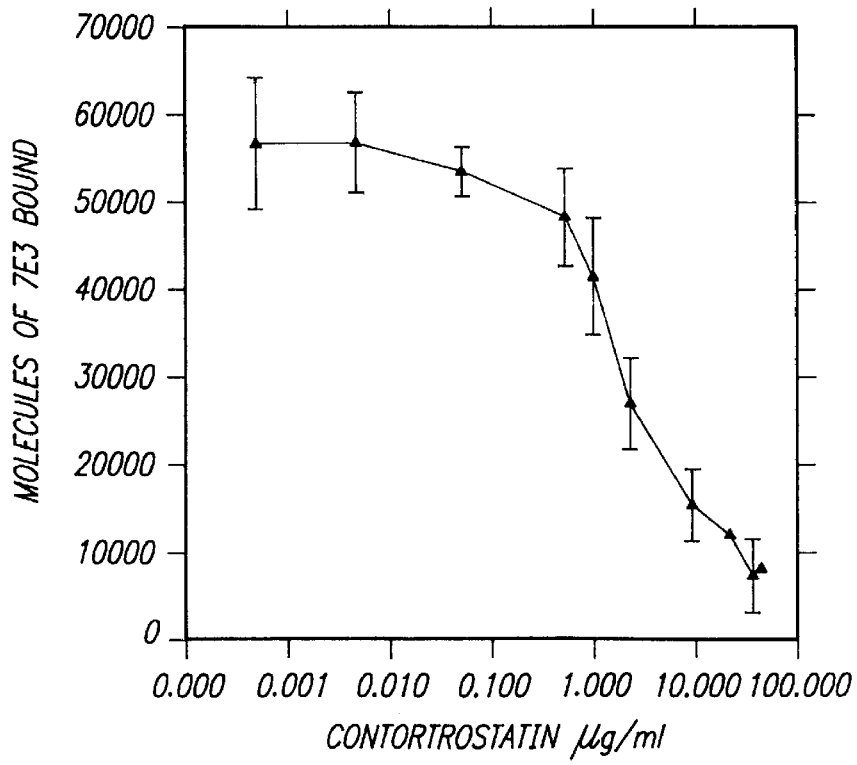

The competitive binding studies using 7E3 demonstrated specific platelet GPIIb/IIIa receptor binding for CN with both human (FIG. 12A) and canine (FIG. 12B) platelets. The concentration of CN to inhibit 50% of 7E3 binding to human GPIIb/IIIa ($IC_{50}$) is 0.4 $\mu$g/ml (27 nM). The $IC_{50}$ for CN for canine GPIIb/IIIa is 0.24 $\mu$g/ml (16 nM). These studies confirm that CN inhibits platelet aggregation by binding to GPIIb/IIIa.

EXAMPLE 10
In Vivo Thrombolytic Efficacy of CN

CN has been studied in a reoccluding canine model of arterial thrombosis. The protein was studied initially by systemic infusion at different dosages to determine its relative potency. This data has permitted an assessment of the systemic dose needed for effective antithrombotic (antiplatelet) activity. The effects upon physiological parameters and circulating coagulation factors have also been monitored.

The model of carotid artery thrombosis in the anesthetized canine described is a modification of one developed for the study of experimentally-induced coronary artery thrombosis [Romson, J. L. et al., Thromb. Res. 17:841 (1980)]. The experimental procedure results in the formation of a platelet rich intravascular thrombus at the site of an electrolytically-induced endothelial lesion in proximity to a distal arterial stenosis. The carotid artery is selected for the experimental model, thereby allowing one vessel to be used as a control and the other to be used after administration of the thrombolytic and antithrombotic therapy. APSAC (anisoylated plasminogen streptokinase activator complex) has been used as the thrombolytic agent successfully in this model. The carotid artery response to the electrolytic injury is similar to that observed in the canine coronary artery but has the advantage of each dog demonstrating the ability to form bilateral occlusive thrombi. The lytic-antithrombotic combination of agents may then be administered to only one of the occluded vessels; this allows for an internal control and eliminates those animals that may not form thrombi due to causes unrelated to the vessel wall injury and subsequent occlusive thrombus formation, i.e., low circulating platelet counts, enhanced spontaneous thrombolysis, presence of heart worms, etc. Parameters which are recorded include repeated measures of: phasic and mean carotid artery blood flow velocity using an ultrasonic flow probe, time to thrombotic occlusion, time to recanalization, ex vivo platelet aggregation, prothrombin time, thrombin time, activated partial thromboplastin time, red cell and white cell counts, hematocrit, EKG profile and body temperature, before and after administration of APSAC or APSAC plus CN to separate groups of animals.

Figure 13:
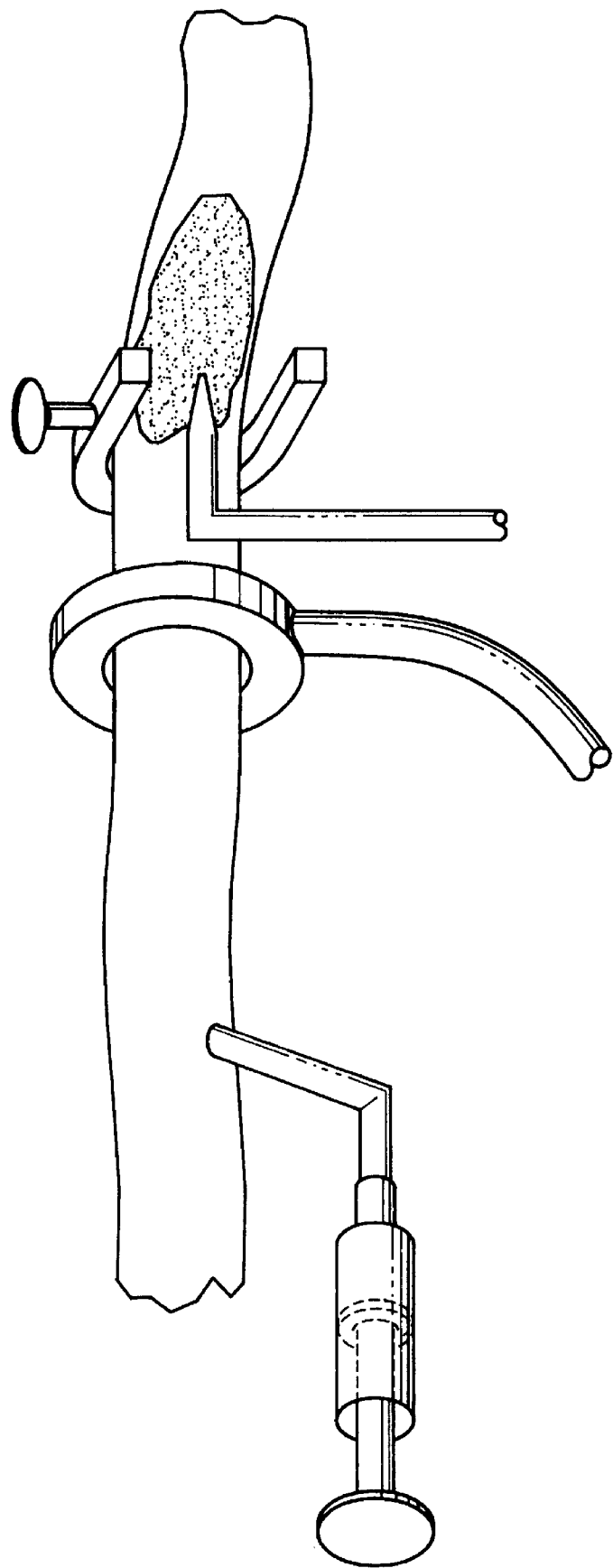
FIG. 13 is a schematic representation of an instrumented canine carotid artery showing placement of an ultrasonic flow probe, mechanical constrictor (stenosis) and intracarotid anodal electrode for inducing intimal injury to the vessel wall to initiate thrombus formation.

Conditioned male mongrel dogs (8–10 kg) have been used for all in vivo studies. Dogs are anesthetized with sodium pentobarbital, intubated and allowed to breath room air under positive pressure respiration. Arterial blood gasses and pH determinations are made every 45 minutes and appropriate adjustments made to maintain the blood gasses and arterial pH within normal limits. Both common carotid arteries and the right internal jugular vein are exposed. A catheter is inserted into the jugular vein for blood sampling and administration of the test drug. Arterial blood pressure is monitored from the cannulated femoral artery with the use of a blood pressure transducer. A Doppler flow probe is placed on each common carotid artery proximal to both the point of insertion of the intraarterial electrode and the mechanical constrictor. The constrictor is adjusted until the pulsatile flow pattern is reduced by 50% without altering mean blood flow. Blood flow velocity in the carotid vessels is monitored continuously. FIG. 13 is a schematic representation of the instrumentation of the carotid artery.

Electrolytic injury to the intimal surface of each carotid vessel is accomplished with the use of an intravascular electrode. Each intraarterial electrode is connected to the positive pole (anode) of a dual channel stimulator. The cathode is connected to a distant subcutaneous site. The current delivered to each vessel is monitored continuously and maintained at 300 $\mu$A. The anodal electrode is positioned to have the uninsulated portion in intimate contact with the endothelial surface of the vessel. Proper positioning of the electrodes in each of the carotid arteries is confirmed by visual inspection at the end of each experiment. The anodal current is applied for a maximum period of 3 hours or is terminated 30 minutes after blood flow in the involved vessel remains stable at zero flow velocity to verify having achieved formation of a stable occlusive thrombus. The right carotid artery serves as the control vessel, whereas the left carotid artery serves as the test vessel. Vessel wall injury is induced simultaneously in each carotid artery.

APSAC (0.05 U/kg) is infused as a bolus proximal to the thrombus in the left carotid artery only. The dose of APSAC has been determined as one that will consistently lyse the locally injected carotid thrombus without producing a systemic lytic effect. Thus, lysis in the uninjected right carotid should not occur. CN is given intravenously in a 10% bolus immediately following APSAC and the remaining 90% is infused over 1 hour. CN dosages ranged from 0.155 to 0.40 mg/kg; the agent was dissolved at the appropriate dose in a volume of 20 ml of sterile saline for infusion. Reperfusion is defined as the restoration of carotid artery blood flow velocity to 20% of baseline values. Patency is defined as measurable carotid artery flow velocity. Blood pressure, heart rate, and carotid artery flow velocity are monitored for 6 hours or until rethrombosis occurs.

Blood (20 ml) was withdrawn for platelet studies from the jugular cannula into a plastic syringe containing 3.2% sodium citrate as anticoagulant (1/10 citrate/blood, vol/vol). Blood was taken for platelet aggregation and whole blood cell counts at baseline 60, 120, 180, 240 and 300 minutes after the administration of CN. The platelet count was determined with a cell counter. Platelet rich plasma, the supernate present after centrifugation of anticoagulated whole blood at 140×g for 5 minutes, was diluted with platelet poor plasma to achieve a platelet count of 200,000/$mm^3$. Platelet poor plasma was prepared after the platelet rich plasma was removed, by centrifuging the remaining blood at 12,000×g for 10 minutes and discarding the bottom cellular layer. Ex vivo platelet aggregation was measured by established spectrophotometric methods with a four channel aggregometer by recording the increase in light transmission through a stirred suspension of platelet rich plasma maintained at 37° C. Aggregation was induced with arachidonic acid (0.65 mM and 0.325 mM) and ADP (20 $\mu$M and 5 $\mu$M).

A subaggregatory dose of adrenaline (550 nM) was used to prime the platelets before stimulation. Values are expressed as percentage of aggregation, representing the percentage of light transmission standardized to platelet rich and platelet poor plasma samples yielding 0% and 100% of light transmission, respectively.

At the conclusion of the study protocol each vessel segment is ligated, proximal and distal to the point of injury, and removed without disturbing the intravascular thrombus. The vessel segment is opened and the intact thrombus is lifted off and weighed.

Five animals have been studied thus far with CN plus APSAC, six with APSAC alone, and a positive control group of six dogs with APSAC plus 7E3 anti-GPIIb/IIIa monoclonal antibody. There were essentially no changes in mean arterial blood pressure or mean heart rate following infusion of CN. Further, the carotid artery flow velocity stayed at a high level following infusion of APSAC plus CN as compared to APSAC infusion alone. In the group of animals infused with APSAC alone, the carotid artery opened for a few minutes following infusion of the lytic agent but then reoccluded and remained closed for the duration of the study. In the positive control group, the animals were infused with APSAC (0.1 U/kg) intraarterially and this was followed by a bolus of 7E3 anti-GPIIb/IIIa F(ab')2 (0.8 mg/kg). In these six animals, the carotid artery remained open following infusion of the combination of APSAC and 7E3 and remained open until the conclusion of the experimental protocol. In the group of five animals infused with APSAC plus CN the results were essentially the same as with the combination of 7E3 and APSAC. However, Table 1 reveals that there was a significant advantage to the combination of APSAC plus CN in terms of the residual thrombus weight. In Table 2, CTTX=CN and RCA=right carotid artery. In the group of five animals treated with this combination of agents the residual thrombus weight per kg dog weight was 1.5, versus 2.4 in the six animals in the APSAC plus 7E3 group, and 4.1 in the APSAC alone group (six animals). Finally, in one of the dogs treated with APSAC plus CN (0.155 mg/kg) platelet aggregation and platelet counts were followed (FIG. 14); CN infusion began at time 0 and was continued for 60 minutes thereafter.

TABLE 2

Weight of Residual Thrombus in Canine Carotid Artery Thrombosis Model

| | APSAC Control | | APSAC & 7E3 | | APSAC & CTTX | |
|---|---|---|---|---|---|---|
| Dog # | Dog Weight (kg) | RCA Thrombus (mg) | Dog Weight (kg) | RCA Thrombus (mg) | Dog Weight (kg) | RCA Thrombus (mg) |
| 1 | 19.2 | 27.3 | 9.4 | 37.3 | 15.2 | 16.8 |
| 2 | 6.5 | 47.6 | 12.2 | 37.5 | 8.2 | 19.2 |
| 3 | 18.2 | 90.5 | 17 | 53.2 | 9.2 | 3.5 |
| 4 | 20.2 | 60.1 | 11.6 | 3.2 | 8.5 | 33.1 |
| 5 | 16.8 | 67.5 | 8.6 | 36.5 | 9 | 15.1 |
| 6 | 10 | 78.5 | 15.9 | 11.8 | | |
| Mean | 15.2 | 61.9 | 12.5 | 29.9 | 10 | 14.6 |
| SEM | 2.1 | 8.4 | 1.4 | 7.6 | 1.4 | 4.9 |
| Thrombus weight per kg | | 4.1 | | 2.4 | | 1.5 |

These results are typical of those in dogs in this group. It can be seen that platelet aggregation was compromised by treatment with the venom protein, but that there appeared to be a return of aggregation at the conclusion of the experiment. Similarly, the platelet count was also depressed during the course of the experiment. It is suspected that the platelets are sequestered in some sanctuary such as the spleen and are then released following a short residence time; platelets returning into the circulation appear to be functional. There is a drop in platelet counts to 10–20% of the baseline value, with recovery to 30–40% by the conclusion of the experimental procedure. Platelet aggregability fluctuates somewhat due to the low platelet count; however, it can be seen that platelet aggregability in the residual platelets appears to be returning to normal at the conclusion of the experimental procedure.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

We Claim:

1. A method of preventing tumor metastasis and neovascularization in a cancer patient suffering from melanoma, carcinoma, or sarcoma, comprising administering contortrostatin to said patient in the amount effective to prevent metastasis.

2. The method of claim 1 in which said cancer patient is a breast cancer patient.

3. The method of claim 1 wherein the contortrostatin is administered to the said patient in the amount effective to inhibit binding of integrin receptors to vitronectin.

* * * * *

UNITED STATES PATENT AND TRADEMARK OFFICE
CERTIFICATE OF CORRECTION

PATENT NO. : 5,814,609

DATED : September 29, 1998

INVENTOR(S) : Francis S. Markland, Jr. et al.

It is certified that error appears in the above-identified patent and that said Letters Patent is hereby corrected as shown below:

| Column | Line | |
|---|---|---|
| 1 | 6 | Change "continuatio" to -- continuation -- |
| 1 | 9 | Before "8" insert -- 0 -- |
| 1 | 10 | Before "8" insert -- 0 -- |
| 1 | 26 | Change "beast" to -- breast -- |
| 1 | 65 | Change "submits" to -- subunits -- |
| 2 | 14 | Change "GPIIb/IIIa" to -- (GP) IIb/IIIa -- |
| 2 | 20 | Change "Crotalidae" to -- *Crotalidae* -- |
| 2 | 20 | Change "Viperidae" to -- *Viperidae* -- |
| 2 | 24 | Change "fibtinolysis" to -- fibrinolysis -- |
| 2 | 61 | Change "cannatus" to -- carinatus -- |
| 3 | 1 | Change "bistatin" to -- bitistatin -- |
| 3 | 7 | Delete "20" |
| 3 | 18 | Change "trigamin" to -- trigramin -- |
| 3 | 21 | Change "Trigamin" to -- Trigramin -- |
| 3 | 23 | Change "Trigamin" to -- Trigramin -- |
| 3 | 26 | Change "$10^{-4}M$" to -- $10^{-8}M$ -- |
| 3 | 31 | Change "*Chemn.*" to -- *Chem.* -- |
| 3 | 36 | Change "disulified" to -- disulfide -- |
| 3 | 51 | After "$10^5$" and before "mm" insert -- / -- |
| 4 | 26 | Change "HT1080" to -- HT-1080 -- |
| 5 | 5 | Delete "30" |
| 5 | 42 | Change "in vitro" to -- *in vitro* --; after "*vitro*" delete " . " and insert -- ; -- |

UNITED STATES PATENT AND TRADEMARK OFFICE
CERTIFICATE OF CORRECTION

PATENT NO.   : 5,814,609
DATED        : September 29, 1998
INVENTOR(S)  : Francis S. Markland, Jr. et al.

It is certified that error appears in the above-indentified patent and that said Letters Patent is hereby corrected as shown below:

| Column | Line | |
|---|---|---|
| 5 | 47 | Change "(FIG. 2A)" to -- (FIG. 12A) -- |
| 5 | 47 | Change "(FIG. 2B)" to -- (FIG. 12B)-- |
| 6 | 3 | Delete "20" |
| 6 | 7 | Before "precursor" insert -- and its -- |
| 6 | 7 | Change "[seq ID NO=1]" to -- [SEQ ID NO:1] -- |
| 7 | 56 | Change "µg/gday" to -- µg/day -- |
| 8 | 24 | Change "preliminary" to -- preliminarily -- |
| 8 | 47 | Change " , "to -- ; -- |
| 8 | 53, 54 | Change "In Vitro" to -- *In Vitro* -- |
| 8 | 55 | Change "m]" to -- ml -- |
| 8 | 58, 59 | Change "in vitro" to -- *in vitro* -- |
| 8 | 64 | Change "in vitro" to -- *in vitro* -- |
| 8 | 65 | Change "In Vivo" to -- *In Vivo* -- |
| 9 | 20 | Change "in vitro" to -- *in vitro* -- |
| 9 | 57 | Change "in vivo" to -- *in vivo* -- |
| 11 | 54 | Delete "20" |
| 15 | 16 | Change "GPIIb/HIa" to -- GPIIb/IIIa -- |
| 15 | 20 | Change "In Vivo" to -- *In Vivo* -- |
| 15 | 55 | Change "ex vivo" to -- *ex vivo* -- |
| 15 | 62 | Change "in vivo" to -- *in vivo* -- |
| 16 | 62 | Change "Ex vivo" to -- *Ex vivo* -- |

UNITED STATES PATENT AND TRADEMARK OFFICE
CERTIFICATE OF CORRECTION

PATENT NO. : 5,814,609
DATED : September 29, 1998
INVENTOR(S) : Francis S. Markland, Jr. et al.

It is certified that error appears in the above-indentified patent and that said Letters Patent is hereby corrected as shown below:

| Column | Line | |
|--------|------|---|
| 22 | 14 | Delete the first occurrence of "the"; change the second occurrence of "the" to -- an --. |

Signed and Sealed this

Twenty-eighth Day of September, 1999

Attest:

Q. TODD DICKINSON

Attesting Officer

Acting Commissioner of Patents and Trademarks